United States Patent [19]
Burpee et al.

[11] Patent Number: 5,913,895
[45] Date of Patent: Jun. 22, 1999

[54] INTRAVASCULAR STENT WITH ENHANCED RIGIDITY STRUT MEMBERS

[75] Inventors: Janet W. Burpee; David R. Fischell, both of Fair Haven, N.J.

[73] Assignee: IsoStent, Inc., Belmont, Calif.

[21] Appl. No.: 08/867,488

[22] Filed: Jun. 2, 1997

[51] Int. Cl.⁶ ..................................................... A61F 2/06
[52] U.S. Cl. ................................. 623/1; 623/12; 606/191; 606/198
[58] Field of Search .......................... 623/1, 12; 606/191, 606/198

[56] References Cited

U.S. PATENT DOCUMENTS

| | | | |
|---|---|---|---|
| 5,383,892 | 1/1995 | Cardon et al. | 623/12 |
| 5,449,373 | 9/1995 | Pinchasik et al. | 623/1 |
| 5,601,593 | 2/1997 | Freitag | 623/12 |
| 5,607,442 | 3/1997 | Fischell et al. | 623/12 |
| 5,632,840 | 5/1997 | Campbell | 623/1 |
| 5,693,089 | 12/1997 | Inoue | 623/12 |
| 5,697,971 | 12/1997 | Fischell et al. | 623/1 |
| 5,733,303 | 3/1998 | Israel et al. | 623/1 |
| 5,741,327 | 4/1998 | Frantzen | 623/1 |
| 5,755,776 | 5/1998 | Al-Saadon | 623/1 |
| 5,755,781 | 5/1998 | Jayaraman | 623/1 |

*Primary Examiner*—Paul B. Prebilic

[57] ABSTRACT

Disclosed herein is a thin-walled cylindrical stent in which one or more of the sets of strut members are more radially rigid after stent expansion as compared to other sets of strut members. Each set of strut members consists of a multiplicity of structural struts that are connected together with the struts extending circumferentially when the stent is outwardly radially deployed within a vessel of a human body. The sets of strut members are those parts of the stent which unfold during radial expansion and provide the radially rigid structure which maintains vessel patency. This invention is a stent structure specifically designed to have enhanced radial rigidity either at the ends or the center of the stent. More radially rigid end struts reduce injury to the vessel from over expansion at the ends of the stent. The embodiment of the present invention with enhanced rigidity in the center would be particularly useful for the treatment of calcified obstructions. Enhanced rigidity can be achieved by either having a set of strut members that becomes more ring-like when radially deployed, or the strut members have a greater width as compared to other strut members of the stent.

14 Claims, 6 Drawing Sheets

INTRAVASCULAR STENT WITH ENHANCED RIGIDITY STRUT MEMBERS

FIELD OF USE

This invention is in the field of intravascular stents that are used to maintain patency of a blood vessel.

BACKGROUND OF THE INVENTION

It has been shown that intravascular stents are an excellent means to maintain the patency of blood vessels following balloon angioplasty. Palmaz in U.S. Pat. No. 4,733,665 describes a balloon expandable slotted tube stent. This and other designs currently known in the art would have fairly uniform stent rigidity except at the ends where the stent is typically weaker.

The weakness at the end can cause over expansion of the end struts, which can increase injury to the vessel wall. The more the injury, the greater the neointimal hyperplasia and the probability of reclosing of the stent within 6 months following implantation.

Ostial obstructions such as those that often occur at the junction of the aorta and renal artery are difficult to treat with standard angioplasty balloons or stents. Ostial lesions tend to exhibit extreme elastic recoil which makes balloon angioplasty ineffective. Enhanced end strength would be of great value for treating ostial lesions.

On the other hand, calcified obstructions may require enhanced rigidity in the center section of the stent.

SUMMARY OF THE INVENTION

This invention describes a stent structure specifically designed to have enhanced radial rigidity at the ends and/or in the center. This invention also will provide a stent structure which should reduce injury to the vessel from over expansion of the stent end struts. It is also specifically designed to be able to maintain the patency of lesions such as renal artery ostial obstructions or the ostium of bypass grafts where they are attached to the aorta. The embodiment of the present invention with enhanced rigidity in the center would be particularly useful for the treatment of calcified obstructions.

The present invention is a specially designed stent in which one or more of the sets of strut members are more radially rigid after stent expansion as compared to other sets of strut members. Each set of strut members consists of a multiplicity of structural struts that are formed from a single piece of metal. Each set of strut members extends circumferentially around the stent in the form of a closed ring. The sets of strut members are the part of a stent which unfold during expansion and provide the radially rigid structure which maintains vessel patency.

Thus an object of this invention is to have a stent with the ends having equal or greater radial rigidity compared to the remainder of the stent.

Still another object of this invention is to have a stent with sets of end struts having reduced flare out during expansion.

Another object of this invention is to have a stent with a centrally located section having greater radial rigidity than the remainder of the stent.

Yet another object of this invention is to have a stent with end struts which approximate rings at the maximum stent expansion diameter.

Still another object of this invention is to have a stent with both the ends and the center having greater radial rigidity than the remainder of the stent.

These and other objects and advantages of this invention will become obvious to a person of ordinary skill in this art upon reading of the detailed description of this invention including the associated drawings as presented herein.

DETAILED DESCRIPTION OF THE DRAWINGS

Figure 1:
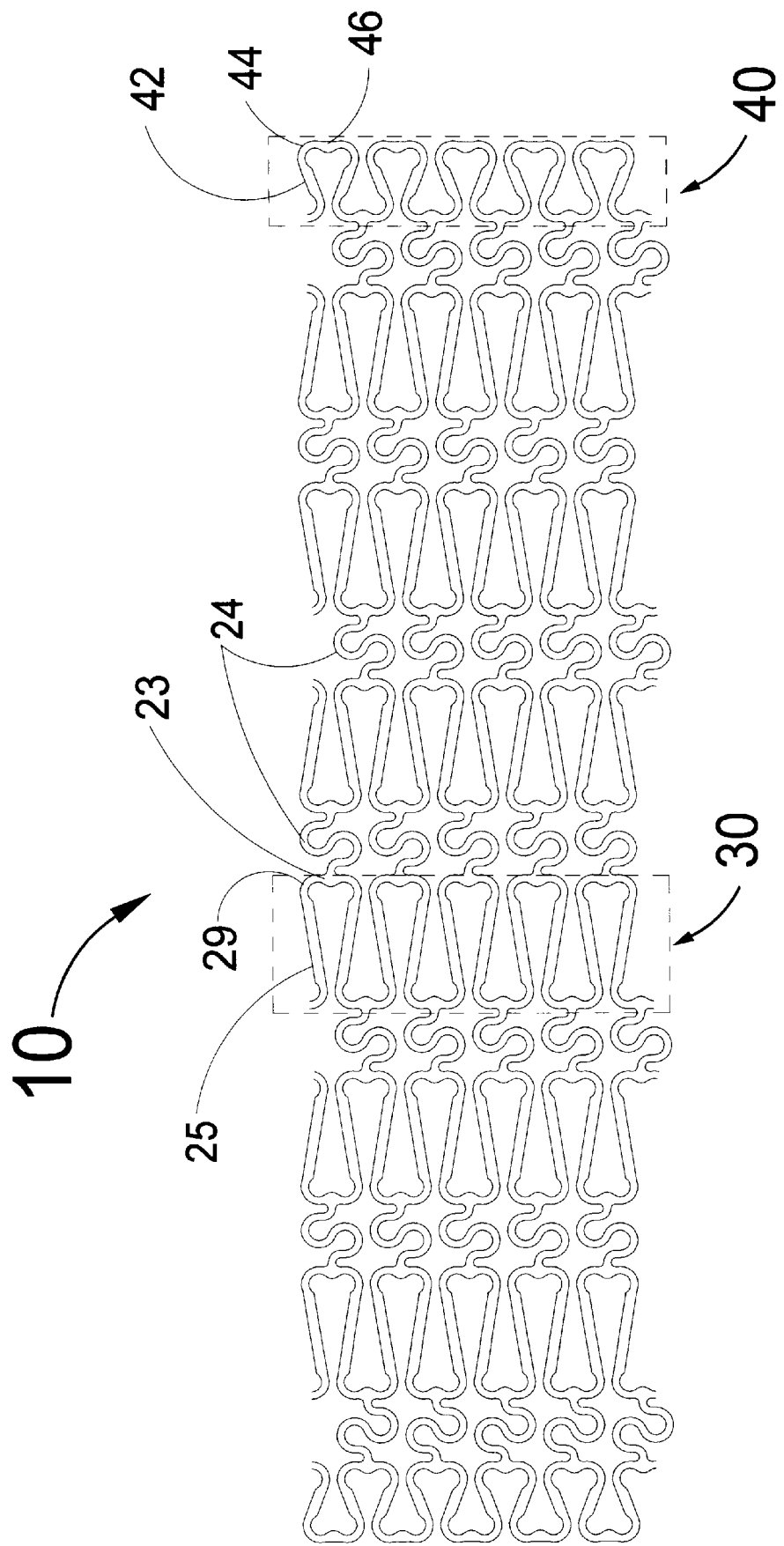
FIG. 1 is a flat lay out view of an undeployed stent which will have increased radial rigidity at the ends of the stent when deployed.

FIG. 1 is a flat lay out view of a strong end (increased radial rigidity at the ends) stent 10 in its pre-deployment state. The strong end stent 10 is typically laser cut from a stainless steel tube with sets of standard strut members 30 and sets of end strut members 40. The sets of standard strut members 30 comprising diagonal struts 25 with curved end sections 29 joined by circumferential struts 23. The sets of end strut members 40 comprising shortened diagonal struts 42 with curved end sections 44 joined by circumferential struts 46. The sets of standard and end strut members 30 and 40 are the part of the stent 10 which unfold during expansion and provide the radially rigid structure which maintains vessel patency.

The sets of standard strut members 30 are connected to each other and to the sets of end strut members 40 with sets of longitudinal "S" undulations 24. The "S" undulations 24 provide increased flexibility by their ability to readily contract or expand as the pre-deployed stent 10 mounted on a balloon catheter (not shown) negotiates a bend in a curved vessel.

Although FIG. 1 shows the stent 10 with a single set of end strut members 40 at each end, two or more sets of end strut members 40 could be placed side by side to further enhance the rigidity at the ends of the stent 10.

Although "S" shaped undulations 24 are shown here, it is also envisioned that either one half of an "S" ( a "U") or "S" and "U" undulations connected together or in any combination could also enhance the flexibility of the strong end stent 10 of the present invention. Although five "S" shaped undulations 24 are shown here connecting adjacent sets of strut members, it is also envisioned that to further increase stent longitudinal flexibility, fewer than five "S" shaped undulations 24 could be used to connect adjacent sets of strut members.

Figure 2:
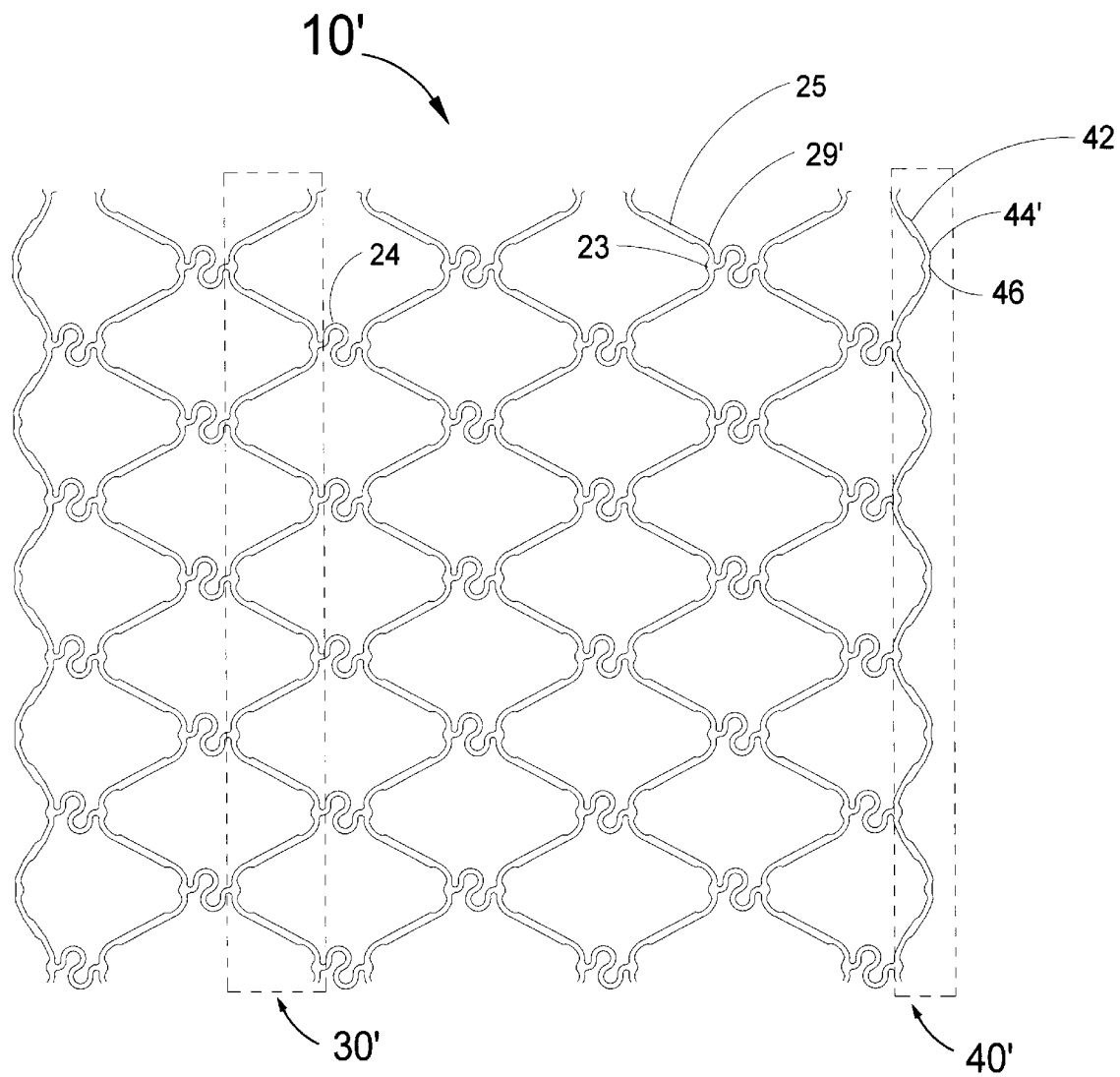
FIG. 2 is a flat lay out view of the stent design in FIG. 1 in its deployed state.

FIG. 2 is a flat lay out view of the strong end stent 10' in its deployed state having deployed sets of standard and end strut members 30' and 40'. In FIG. 1 the sets of end strut members 40 have a shorter length in the longitudinal direction as compared to the standard strut members 30. This shorter length causes the sets of end strut members 40 to have a more "ring-like" shape with an associated enhanced rigidity when expanded as compared to the sets of standard strut members 30. This can be seen in FIG. 2, which shows the expanded sets of end strut members 40' of the deployed stent 10' having a more ring-like structure as compared to the expanded sets of standard strut members 30'. This more ring-like structure should make the expanded sets of end strut members 40' of the deployed stent 10' more radially rigid than the expanded sets of standard strut members 30'.

Another means to increase the relative radial strength of the sets of end strut members is to increase the strut width of the curved end sections 44 (or 44') of the set of end strut members 40 (40').

Figure 3:
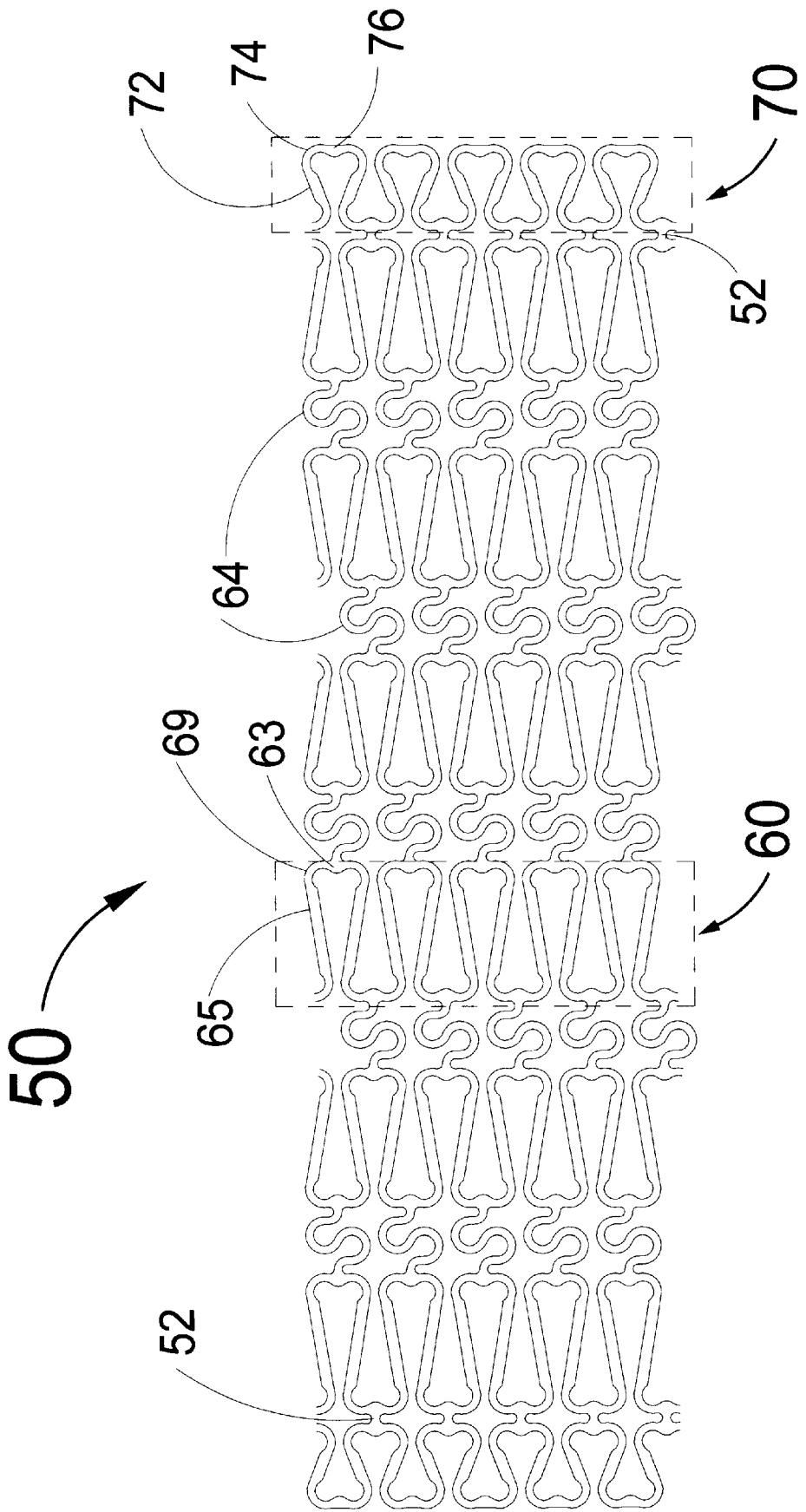
FIG. 3 is an alternate embodiment of the stent which will have increased radial rigidity at the stent ends when deployed.

FIG. 3 is a flat lay out view of an alternate embodiment of a strong end stent 50. The strong end stent 50 is typically laser cut from a stainless steel tube with sets of standard strut members 60 and sets of end strut members 70. The sets of standard strut members 60 comprising diagonal struts 65 with curved end sections 69 joined by circumferential struts 63. The sets of end strut members 70 comprising shortened diagonal struts 72 with curved end sections 74 joined by circumferential struts 76. The sets of standard and end strut members 60 and 70 are the part of the stent 50 which unfold during expansion and provide the radially rigid structure which maintains vessel patency.

In this embodiment, the sets of end strut members 70 are connected to the adjacent set of standard strut members 60 with longitudinal "H" cross bars 52. With "H" cross bars 52 as opposed to "S" undulations as shown in FIG. 1, the sets of end strut members 70 will be closer and more rigidly connected to the adjacent sets of standard strut members 60 and the radial strength of the ends of the stent 50 after expansion will be increased further. Although five "H" cross bars 52 are shown here connecting adjacent sets of end and standard strut members, 70 and 60, it is also envisioned that to increase stent longitudinal flexibility, fewer than five "H" cross bars 52 could be used to connect adjacent sets of end and standard strut members, 70 and 60.

Figure 4:
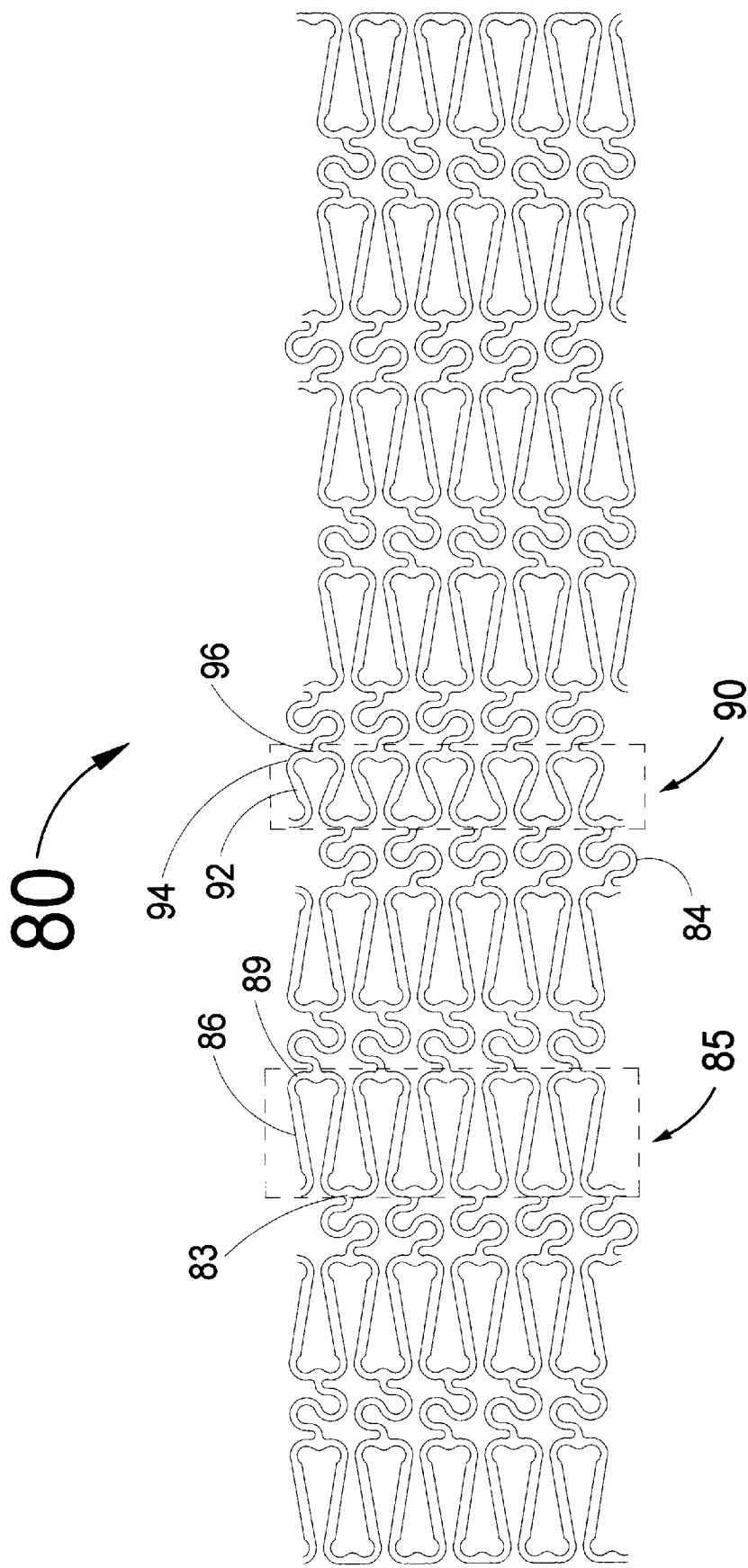
FIG. 4 is a flat lay out view of an undeployed stent which will have increased radial rigidity at the center of the stent when deployed.

FIG. 4 is a flat lay out view of an undeployed strong center stent 80 in its pre-deployed state. The strong center stent 80 is typically laser cut from a stainless steel tube with sets of standard strut members 85 and a set of central strut members 90. The sets of standard strut members 85 comprising diagonal struts 86 with curved end sections 89 joined by circumferential struts 83. The set of central strut members 90 comprising shortened diagonal struts 92 with curved end sections 94 joined by circumferential struts 96. The sets of standard and central strut members 85 and 90 are the part of the stent 80, which unfold during expansion and provide the radially rigid structure which maintains vessel patency.

The sets of standard strut members 85 are connected to each other and to the set of central strut members 90 with sets of longitudinal "S" undulations 84. The "S" undulations 84 provide increased flexibility by their ability to readily contract or expand as the pre-deployed stent 80 mounted on a balloon catheter (not shown) negotiates a bend in a curved vessel.

Although FIG. 4 shows the stent 80 with a single set of central strut members 90, two or more sets of central strut members 90 could be placed side by side to further enhance the rigidity at the center of the stent 80.

Although "S" shaped undulations 84 are shown here, it is also envisioned that either one half of an "S" ( a "U") or "S" and "U" undulations connected together or in any combination could also enhance the flexibility of the strong center stent 80 of the present invention.

In FIG. 4 the set of central strut members 90 has a shorter length in the longitudinal direction as compared to the sets of standard strut members 85. This shorter length causes the set of central strut members 90 to have a more "ring like" shape with enhanced radial rigidity when expanded as compared to the sets of standard strut members 85. This is clearly seen in FIG. 5 which shows the deployed stent 80'.

Figure 5:
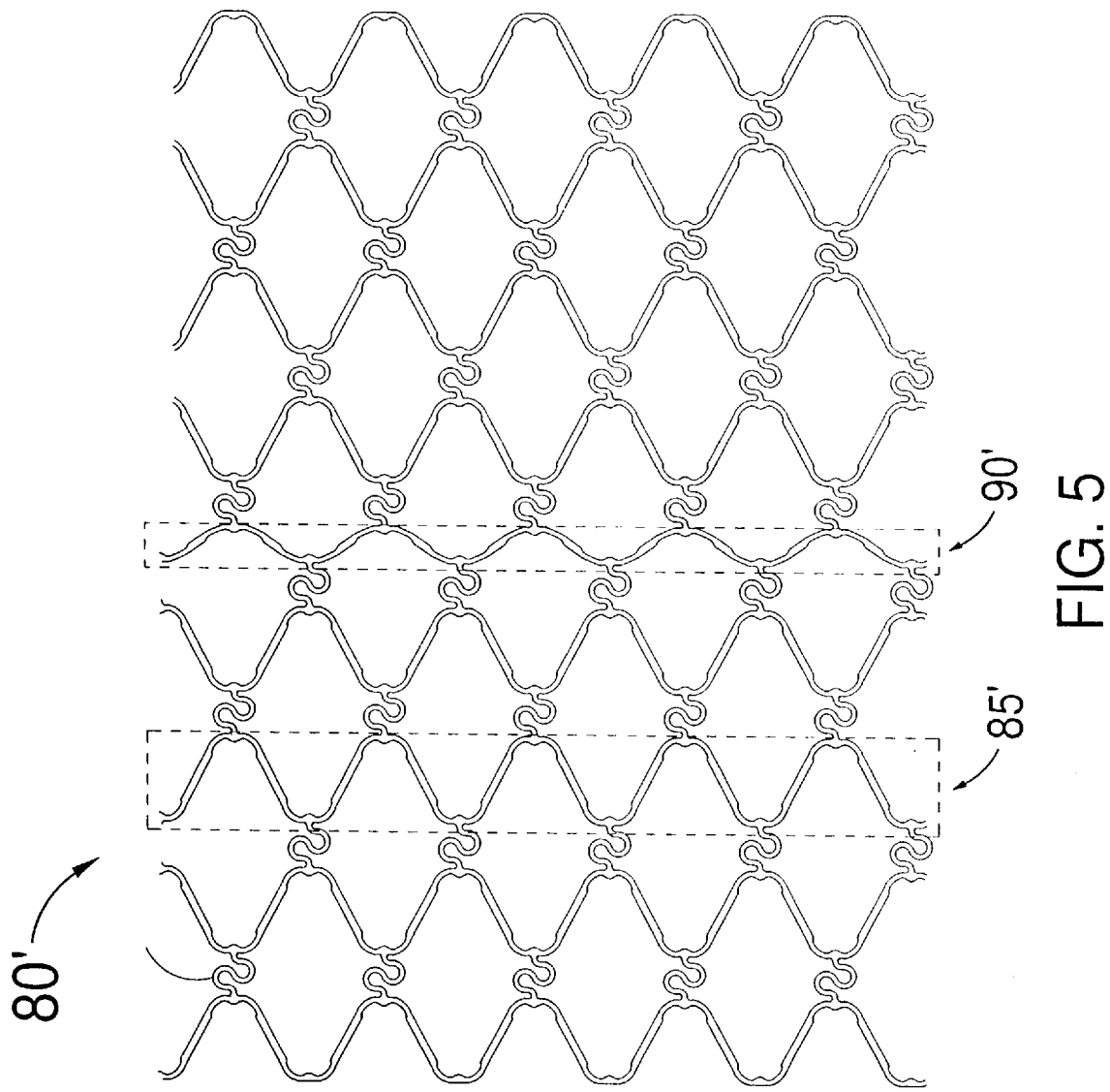
FIG. 5 is a flat lay out view of the stent of FIG. 4 in its deployed state.

FIG. 5 is a flat lay out view of a strong center stent 80' in its deployed state having deployed sets of standard and central strut members 85' and 90'. It should be noted here that, in the expanded state, the shape of the set of central strut members 90' is closer to that of a ring and hence more radially rigid than the expanded sets of standard strut members 85'.

Figure 6:
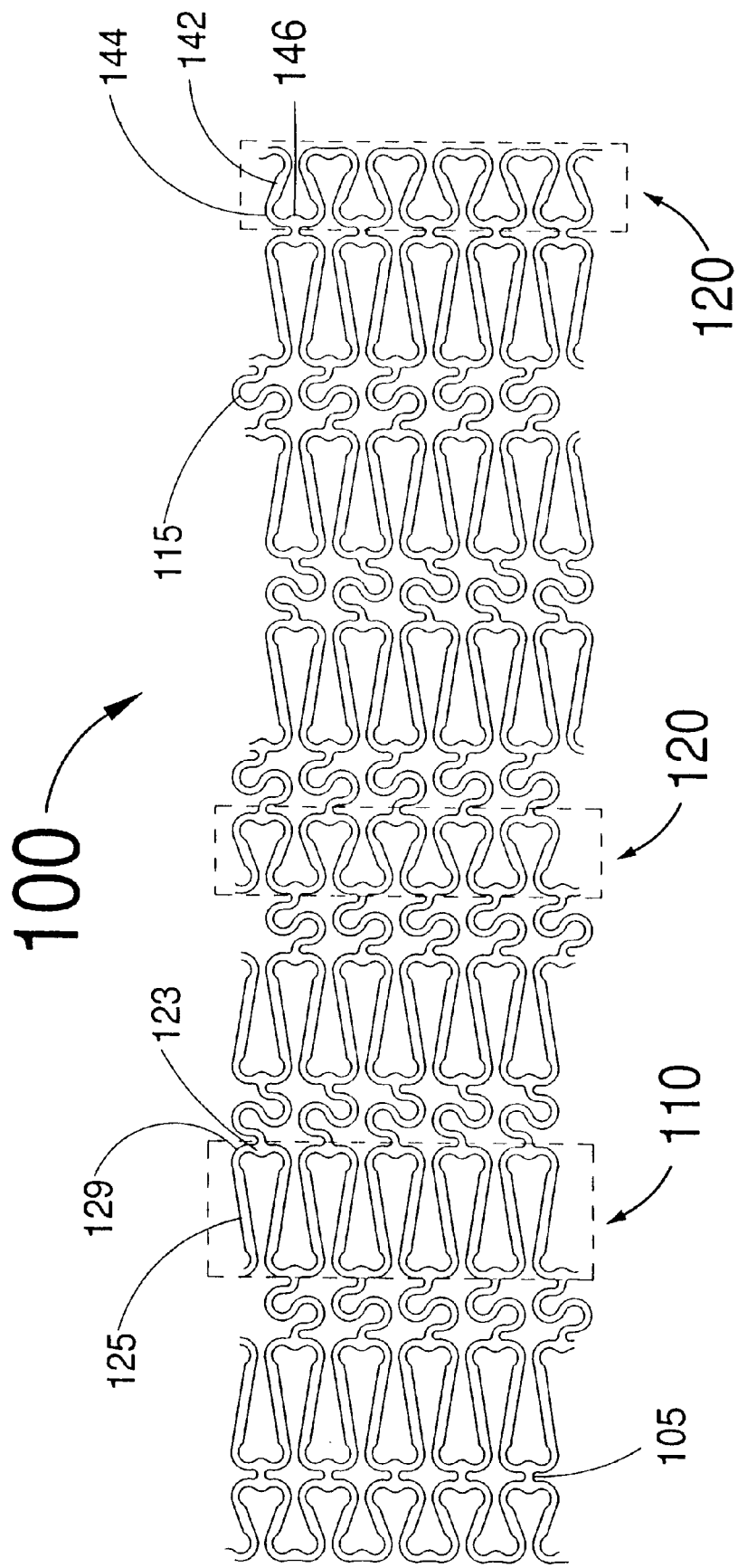
FIG. 6 is a flat lay out view of an undeployed stent which will have increased radial rigidity at both the center and the ends of the strut when deployed.

FIG. 6 is a flat lay out view of an undeployed stent 100 with both strong ends and center. The stent 100 is typically laser cut from a stainless steel tube with sets of standard strut members 110 and sets of strong strut members 120. The sets of standard strut members 110 comprising diagonal struts 125 with curved end sections 129 joined by circumferential struts 123. The sets of strong strut members 120 comprising shortened diagonal struts 142 with curved end sections 144 joined by circumferential struts 146. The sets of standard and strong strut members 110 and 120 are the part of the stent 100 which unfold during expansion and provide the radially rigid structure which maintains vessel patency. In this embodiment, the sets of strong strut members 120 are located at the proximal end, center and distal end of the stent 110. The sets of standard strut members 110 are connected to each other and to adjacent sets of strong strut members with either "H" cross bar links 105 or "S" undulations 115.

Although in this embodiment the "H" crossbar links 105 are used only to connect the adjacent sets of standard and strong strut members 110 and 120, at the distal and proximal ends of the stent 100, it is envisioned that "H" cross bar links 105 could be used in place of "S" undulations for connecting any adjacent sets of strut members.

It is also envisioned that a strong end self-expanding stent made of a material such as Nitinol could be produced and heat treated in the shapes shown in FIGS. 2 or 5 then cooled and folded down to the shapes in FIGS. 1 or 4 for introduction into the human body.

The stents 10, 50, 80 and 100 are ideally laser machined from a tube of metal such as stainless steel or tantalum. Therefore, even though the stents 10, 10', 50, 50', 80, 80' and 100 were shown for the sake of clarity as flat, two dimensional objects, the stents are, of course, thin-walled, cylindrical structures that reach their nominal diameter when fully deployed within a vessel of a human body.

Various other modifications, adaptations, and alternative designs are of course possible in light of the above teachings. Therefore, it should be understood at this time that within the scope of the appended claims the invention may be practiced otherwise than as specifically described herein.

What is claimed is:

1. A thin-walled, cylindrical stent formed from a single piece of metal, the stent having a nominal diameter when fully radially deployed into a vessel of the human body and having a longitudinal direction parallel to the axial axis of the cylindrical stent, the stent further comprising a multiplicity of sets of strut members with each set of strut members forming a circumferentially extending closed ring structure with adjacent sets of strut members being coupled each to the other by structures extending generally in the longitudinal direction, said stent having a proximal end, a distal end and a center section located approximately halfway between said proximal and distal ends, said stent having two types of circumferentially extending sets of strut members, a first type of set of strut members and a second type of set of strut members, the first type of set of strut members having a shorter total circumferential length as compared to the total circumferential length of the second type of set of strut members, the stent when radially deployed to its nominal diameter having the first type of set of strut members having greater radial rigidity as compared to the second type of set of strut members.

2. The stent as recited in claim 1 where said first type of set of strut members has a length in the longitudinal direction that is less than the length in the longitudinal direction of said second type of set of strut members.

3. The stent as recited in claim 1 where said sets of strut members are coupled each to the other by at least two substantially longitudinally extending undulating members.

4. The stent as recited by claim 3 where the substantially longitudinally extending undulating members are formed in an S-shaped contour.

5. The stent as recited by claim 3 where the substantially longitudinally extending undulating members are formed in a U-shaped contour.

6. The stent as recited by claim 1 where there is at least one of the first type of set of strut members situated at said proximal end of the stent.

7. The stent as recited by claim 6 where there is at least one of the first type of set of strut members situated at said distal end of the stent.

8. The stent as recited by claim 1 where there is at least one of the first type of set of strut members situated at said distal end of the stent.

9. The stent as recited by claim 1 where there is at least one of the first type of set of strut members at said center section of the stent.

10. The stent as recited by claim 7 where there is at least one of the first type of set of strut members situated at said center section of the stent.

11. The stent as recited in claim 1 where said first type of set of strut members has an average dimensional strut width of its strut members that is greater than the average dimensional strut width of the strut members of said second type of set of strut members.

12. The stent as recited in claim 1 where at least two adjacent sets of strut members are coupled each to the other by at least two substantially longitudinally extending linearly directed "H" cross bars.

13. The stent as recited in claim 1 where said stent is radially expanded responsive to inflation of a balloon onto which balloon the stent is mounted.

14. The stent as recited in claim 1 where said stent is a radially self-expanding stent.

* * * * *